United States Patent [19]
Weinel

[11] Patent Number: 4,742,229
[45] Date of Patent: May 3, 1988

[54] PNEUMATIC DETECTOR FOR NONDISPERSIVE INFRARED GAS ANALYZERS

[75] Inventor: Johann Weinel, Karlsruhe, Fed. Rep. of Germany

[73] Assignee: Siemens Aktiengesellschaft, Berlin and Munich, Fed. Rep. of Germany

[21] Appl. No.: 877,447

[22] Filed: Jun. 23, 1986

[30] Foreign Application Priority Data

Jun. 28, 1985 [DE] Fed. Rep. of Germany ... 8518894[U]

[51] Int. Cl.$^4$ ............................................. G01N 21/61
[52] U.S. Cl. ...................................... 250/343; 250/344
[58] Field of Search ............... 250/344, 345, 343, 341, 250/339

[56] References Cited

U.S. PATENT DOCUMENTS

| | | | |
|---|---|---|---|
| 2,951,939 | 9/1960 | Luft | 250/344 |
| 3,968,369 | 7/1976 | Luft | 250/344 |
| 3,970,387 | 7/1976 | Faulhaber et al. | 356/51 |
| 4,210,808 | 7/1980 | Miyatake | 250/343 |
| 4,336,453 | 6/1982 | Imaki et al. | 250/344 |

FOREIGN PATENT DOCUMENTS 2325502 12/1974 Fed. Rep. of Germany .
195438 10/1985 Japan ................................ 250/345

OTHER PUBLICATIONS

M. S. Turnbull, "Non-Dispersive Infra-Red Gas Analyzers" *Electronics and Instrumentation* vol. 2, No. 12 (Mar. 1972) pp. 11-15.

Primary Examiner—Janice A. Howell
Assistant Examiner—Constantine Hannaher
Attorney, Agent, or Firm—Kenyon & Kenyon

[57] ABSTRACT

A pneumatic detector for nondispersive infrared gas analyzers comprises two gas-filled chambers disposable one behind the colinearly with a source of infrared radiation and connected to one another by a gas conductive line containing a microflow sensor which generates an electrical signal indicative of the pressure difference between the two chambers. A third chamber is disposed on a side of the two chambers opposite the radiation source and is connected to a second of the two chambers via a gas conductive line. An adjustable aperture stop is arranged between the second and the third gas-filled chambers. The arrangement of chambers and the adjustable aperture stop serve to compensate and reduce to zero a negative cross-sensitivity.

6 Claims, 1 Drawing Sheet

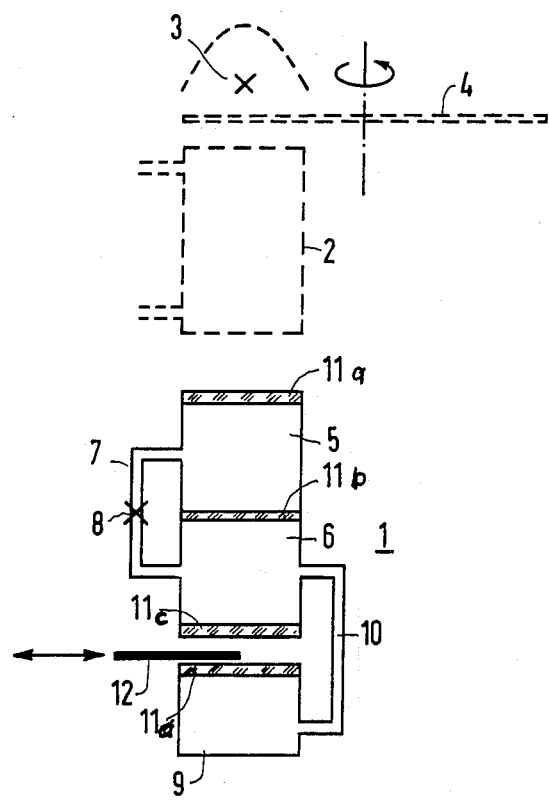

PNEUMATIC DETECTOR FOR NONDISPERSIVE INFRARED GAS ANALYZERS

BACKGROUND OF THE INVENTION

This invention relates to a pneumatic detector for nondispersive infrared (NDIR) gas analyzers.

As disclosed in German Pat. No. 1 017 385, a pneumatic detector for a nondispersive infrared gas analyzer includes two gas-filled detector chambers arranged coaxially one behind the other, the detector chambers being provided with radiation-permeable end faces. The two gas-filled chambers are connected to one another via a gas conductive line containing a pneumatic-electrical converter or transducer sensitive to gas pressure or flow.

In such gas analyzers, the two chambers of the pneumatic detector are disposed colinearly with a source of infrared radiation and with a measurement chamber containing the sample gas mixture. The two detector chambers are disposed on one side of the measurement chamber opposite the source of infrared radiation and contain a gas whose presence in the sample gas mixture is to be analyzed and measured. The subject gas in the two detector chambers is present either in pure form or mixed with a nonabsorbing gas.

Upon passage of infrared radiation from the light source through the measurement chamber and the two detector chambers, pressure increases of different magnitudes arise in the two detector chambers. The gas in the first chamber absorbs radiation of a central portion and of flanking portions of an absorption band, while the gas in the second detector chamber absorbs radiation substantially of the band flanks.

The pneumatic-electrical converter or transducer senses the pressure difference between the gas pressures in the first and second detector chambers and generates a measurement signal corresponding to the detected pressure difference.

In such pneumatic detectors the cross sensitivity caused in the subject gas by overlapping absorption bands of other components is greatly reduced or eliminated. Accordingly, the selectivity of the measurement process is generally increased considerably. However, this increase occurs only if the lengths of the two detector chambers are matched so that approximately the same band edge or band flank radiation is absorbed in both. Inasmuch as the amount of radiation of the band flanks absorbed in the detector chambers can vary in accordance with the kind and absorptivity of the participating gases, it is necessary to adjust the absorption conditions when the subject gas is changed. Because such an adjustment is relatively costly, it is desirable to provide simple means for facilitating quantity production of pneumatic detectors of the above-described type.

An object of the present invention is to provide an improved pneumatic detector of the above-described type.

Another, more particular, object of the present invention is to provide such a pneumatic detector in which adaptation of the detector to different measurement conditions, and particularly to different subject gases, is facilitated.

Another particular object of the present invention is to provide such a pneumatic detector which is simple and easy to manufacture in quantity.

SUMMARY OF THE INVENTION

The present invention is directed to a pneumatic detector for a nondispersive infrared gas analyzer having an infrared light source and a measurement chamber containing a gaseous sample. The pneumatic detector comprises a first detector chamber for containing a first predetermined amount of a selected gas to be analyzed in the sample. A second detector chamber contains a second predetermined amount of the selected gas.

The first and second detector chambers are connected to one another and are disposable colinearly with the infrared light source and the measurement chamber along an axis or radiation path. The second detector chamber is locatable in the aligned configuration on a side of the first detector chamber opposite the light source and the measurement chamber.

The first and the second detector chambers are defined in part by end walls transparent to the infrared radiation emitted by the light source. A first gas conductive line communicates at one end with the first detector chamber and at an opposite end with the second detector chamber. A sensor is disposed in the gas line for generating a signal indicative of a gas pressure in the first detector chamber relative to a gas pressure in the second detector chamber.

A third detector chamber containing a third predetermined amount of the selected gas is disposed colinearly with respect to the first and the second detector chambers on a side of the second chamber opposite the first chamber. The third detector chamber has at least one wall transparent to infrared radiation emitted by the light source, that one wall facing the first and the second detector chambers.

A second gas conductive line communicates at one end with the second detector chamber and at an opposite end with the third detector chamber. A radiation block or stop is arranged between the second detector chamber and the third detector chamber for controlling the amount of infrared radiation entering the third detector chamber from the second detector chamber.

Pursuant to further particular features of the present invention, the radiation block or stop includes an aperture of adjustable size and is provided with a surface which absorbs infrared radiation emitted by the light source.

Pursuant to another particular feature of the present invention, the sum of the heights of the second and third detector chambers, i.e., the dimensions of those chambers parallel to the radiation axis, is greater than the height of the first chamber.

BRIEF DESCRIPTION OF THE DRAWING

The sole FIGURE of the drawing is a schematic diagram of a pneumatic detector in accordance with the present invention.

DETAILED DESCRIPTION

As illustrated in the drawing, a pneumatic detector 1 in accordance with the invention is used in a gas analyzer including a measurement cell or chamber which can be filled with a sample in the form of a gaseous mixture including a selected gas component whose quantity in the gaseous sample is to be determined. Pneumatic detector 1 is disposable colinearly with measurement chamber 2 and a source 3 of infrared radiation which emits a beam of infrared rays interrupted periodically by a rotating interrupter 4.

Pneumatic detector 1, a so-called two layer detector, includes a first detector chamber 5 and a second detector chamber disposable along the radiation path or axis defined by light source 3 and measurement chamber 2. Detector chambers 5 and 6 are each filled, during operation of the device, with a gaseous mixture including the subject gas, i.e., the gas to be measured in the gaseous sample in chamber 2. The subject gas is exemplarily carbon monoxide (CO).

Detector chambers 5 and 6 are connected to one another by a gas conductive line 7, in which a pneumatic-electrical transducer 8 sensitive to gas pressure or flow is disposed. Pneumatic-electrical transducer 8 exemplarily takes the form of a condenser microphone or a flow sensor operating in accordance with the hot wire anemometer principle.

In accordance with the invention, a third detector chamber 9 is disposed behind second detector chamber 6, i.e., on a side of chamber 6 opposite chamber 5, and along the radiation path or axis of the gas analyzer during operation of the device. Third detector chamber 9 is connected to second detector chamber 6 via gas conductive line 10.

The end walls or faces 11a, 11b, 11c and 11d of all three detector chambers 5, 6 and 9 are permeable to the infrared radiation emitted by light source 3.

Between the rear wall or end face 11c of second detector chamber 6 and the forward wall or face 11d of third detector chamber 9 is disposed an aperture stop or block 12 providing an aperture of adjustable size for controlling the amount of infrared radiation entering third detector chamber 9 from second detector chamber 6. The aperture stop 12 advantageously includes a surface, e.g., the surface facing detector chambers 5 and 6, which absorbs infrared radiation emitted by light source 3. Aperture stop 12 is used to adjust the amount of band edge or flank radiation absorbed in chambers 6 and 9 so that that absorbed radiation is approximately equal to the band edge or flank radiation absorbed in first detector chamber 5. The provision of the third detector chamber and the adjustable aperture stop thus enables an avoidance of overcompensation (negative cross-sensitivity)

The heights of second and third detector chambers 6 and 9, i.e., the dimensions of those chambers in a direction parallel to the radiation path or axis, must be designed so that the sum of those heights is larger than the height of first detector chamber 5. It is to be noted that first detector chamber 5 functions as a first receiver layer in the pneumatic detector 1, while second and third detector chambers 6 and 9 together form a second receiver layer.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the descriptions and illustrations herein are proferred by way of example to facilitate comprehension of the invention and should not be construed to limit the scope thereof.

What is claimed is:

1. A pneumatic detector for a nondispersive infrared gas analyzer having an infrared light source and a measurement chamber containing a gaseous sample, said pneumatic detector comprising:

first means in the form of a first detector chamber for containing a first predetermined amount of a selected gas to be analyzed in the sample;

second means in the form of a second detector chamber for containing a second predetermined amount of said selected gas, said first detector chamber and second detector chamber being connected to one another and disposable colinearly along an axis with said infrared light source and said measurement chamber, said second detector chamber being locatable on a side of said first detector chamber opposite said light source and said measurement chamber upon an alignment of said first and said second detector chamber with said light source and said measurement chamber, said first detector chamber and said second detector chamber being defined in part by end walls transparent to infrared radiation emitted by said light source;

a first gas conductive line communicating at one end with said first detector chamber and at an opposite end with said second detector chamber;

sensor means disposed in said gas conductive line for generating a signal indicative of a gas pressure in said first detector chamber relative to a gas pressure in said second detector chamber;

third means in the form of a third detector chamber for containing a third predetermined amount of said selected gas, said third detector chamber being disposed colinearly with respect to said first detector chamber and said second detector chamber and on a side of said second detector chamber opposite said first detector chamber, said third detector chamber having at least one wall transparent to infrared radiation emitted by said light source, said one wall facing said first detector chamber and second detector chamber;

a second gas conductive line separate from said first gas conductive line and communicating at one end with said second detector chamber and at an opposite end with said third detector chamber so that pressure of said selected gas in said third detector chamber is substantially the same as pressure of said selected gas in said second detector chamber; and means disposed between said second detector chamber and said third detector chamber for controlling the amount of infrared radiation entering said third detector chamber from said second detector chamber.

2. The pneumatic detector set forth in claim 1 wherein said means for controlling includes means for providing an aperture of adjustable size.

3. The pneumatic detector set forth in claim 2 wherein said means for providing includes a surface which absorbs infrared radiation emitted by said light source.

4. The pneumatic detector set forth in claim 3 wherein said first detector chamber has a first height dimension parallel to said axis, said second detector chamber has a second height dimension parallel to said axis and said third detector chamber has a third height dimension parallel to said axis, a sum of said second and said third height dimension being greater than said first height dimension.

5. The pneumatic detector set forth in claim 1 wherein said first detector chamber has a first height dimension parallel to said axis, said second detector chamber has a second height dimension parallel to said axis and said third detector chamber has a third height dimension parallel to said axis, a sum of said second and said third height dimension being greater than said first height dimension.

6. In a pneumatic detector for a nondispersive infrared gas analyzer having an infrared light source and a measurement chamber containing a gaseous sample, said pneumatic detector comprising a first chamber and a second chamber for containing respective predetermined amounts of a selected gas to be analyzed in the sample, said first chamber and second chamber being alignable with said infrared light source and said measurement chamber along a radiation path, said first chamber and said second chamber being defined in part by end walls transparent to infrared radiation emitted by said light source, further including a first gas conductive line connected to said first chamber and said second chamber and incorporating transducer means for sensing a difference in pressures of gases in said firs chamber and said second chamber, the improvement comprising:

a third chamber connected to said first and said second detector chamber for containing an additional predetermined amount of said selected gas, said third chamber being disposed colinearly with said first chamber and said second chamber and on a side of said second chamber opposite said first chamber, said third chamber having at least one wall transparent to infrared radiation emitted by said light source, said one wall facing said first chamber and second chamber;

a second gas conductive line separate from said first gas conductive line and communicating at one end with said second chamber and at an opposite end with said third chamber so that pressure of said selected gas in said third chamber is substantially the same as pressure of said selected gas in said second chamber; and means disposed between said second chamber and said third chamber for controlling the amount of infrared radiation entering said third chamber from said second chamber.

* * * * *